(12) United States Patent
Agboh

(10) Patent No.: US 9,869,037 B2
(45) Date of Patent: Jan. 16, 2018

(54) METHOD OF PRODUCING A SWELLABLE POLYMER FIBRE

(71) Applicant: Xiros Limited, Leeds, Yorkshire (GB)

(72) Inventor: Christopher Ochayi Agboh, Leeds (GB)

(73) Assignee: XIROS LIMITED, Leeds (GB)

( * ) Notice: Subject to any disclaimer, the term of this patent is extended or adjusted under 35 U.S.C. 154(b) by 9 days.

(21) Appl. No.: 15/021,625

(22) PCT Filed: Sep. 4, 2014

(86) PCT No.: PCT/GB2014/052666
§ 371 (c)(1),
(2) Date: Mar. 11, 2016

(87) PCT Pub. No.: WO2015/036733
PCT Pub. Date: Mar. 19, 2015

(65) Prior Publication Data
US 2016/0222548 A1 Aug. 4, 2016

(30) Foreign Application Priority Data

Sep. 13, 2013 (GB) .................................... 1316307.6

(51) Int. Cl.
*A61K 9/70* (2006.01)
*A01N 25/34* (2006.01)
(Continued)

(52) U.S. Cl.
CPC ............... *D01F 1/10* (2013.01); *A01N 25/10* (2013.01); *A01N 59/16* (2013.01); *A61L 15/28* (2013.01);
(Continued)

(58) Field of Classification Search
None
See application file for complete search history.

(56) References Cited

U.S. PATENT DOCUMENTS

| | | | |
|---|---|---|---|
| 2,192,194 | A | 3/1940 | Kajita et al. |
| 2,576,576 | A | 11/1951 | Cresswell et al. |

(Continued)

FOREIGN PATENT DOCUMENTS

| | | |
|---|---|---|
| CN | 1978718 | 6/2007 |
| CN | 1986921 | 6/2007 |

(Continued)

OTHER PUBLICATIONS

Qin Y: "Functional alginate fibers", Chemical Fibers International, IBP Press, Frankfurt Am Main, DE, vol. 60, No. 1, Mar. 1, 2010 (Mar. 1, 2010), pp. 32-33, XP001551909, ISSN: 0340-3343.

(Continued)

*Primary Examiner* — Jeffrey T. Palenik
(74) *Attorney, Agent, or Firm* — Kirton McConkie; Evan R. Witt

(57) ABSTRACT

A swellable polymer based fiber and a method of preparing the same optionally comprising glycol, lecithin and optionally an antimicrobial metal species suitable, for example, for medical applications including wound dressings. A method of manufacture may comprise fiber extrusion or spinning involving one or a plurality of in-series coagulation baths to add single or multiple antimicrobial metal species to the as-formed fiber.

10 Claims, 1 Drawing Sheet

(51) Int. Cl.
| | |
|---|---|
| A61K 31/38 | (2006.01) |
| A61K 33/34 | (2006.01) |
| A61K 33/32 | (2006.01) |
| A61K 33/26 | (2006.01) |
| A61K 33/24 | (2006.01) |
| B29C 47/00 | (2006.01) |
| D01F 2/28 | (2006.01) |
| A61K 31/685 | (2006.01) |
| A61K 31/32 | (2006.01) |
| A61K 31/315 | (2006.01) |
| A61K 31/28 | (2006.01) |
| A61K 31/30 | (2006.01) |
| A61K 31/29 | (2006.01) |
| D01F 1/10 | (2006.01) |
| A01N 25/10 | (2006.01) |
| A01N 59/16 | (2006.01) |
| A61L 15/28 | (2006.01) |
| A61L 15/44 | (2006.01) |
| B29C 47/88 | (2006.01) |
| D01F 2/24 | (2006.01) |
| D01F 11/02 | (2006.01) |
| B29K 105/16 | (2006.01) |
| B29K 505/10 | (2006.01) |
| B29K 505/14 | (2006.01) |
| B29L 31/00 | (2006.01) |

(52) U.S. Cl.
CPC .......... *A61L 15/44* (2013.01); *B29C 47/0014* (2013.01); *B29C 47/8895* (2013.01); *D01F 2/24* (2013.01); *D01F 11/02* (2013.01); *A61L 2300/104* (2013.01); *B29K 2005/00* (2013.01); *B29K 2105/16* (2013.01); *B29K 2505/10* (2013.01); *B29K 2505/14* (2013.01); *B29K 2995/0037* (2013.01); *B29L 2031/753* (2013.01)

(56) References Cited

U.S. PATENT DOCUMENTS

| | | | | |
|---|---|---|---|---|
| 5,358,765 | A * | 10/1994 | Markulin | A22C 13/0013 138/118.1 |
| 2003/0017208 | A1* | 1/2003 | Ignatious | A61K 9/70 424/486 |
| 2003/0185863 | A1 | 10/2003 | Bengs et al. | |
| 2012/0040463 | A1 | 2/2012 | Domard et al. | |

FOREIGN PATENT DOCUMENTS

| | | |
|---|---|---|
| CN | 101230150 | 7/2008 |
| CN | 102199810 | 9/2011 |
| EP | 1137827 | 10/2001 |
| EP | 1849464 | 10/2007 |
| GB | 1588647 | 4/1981 |
| GB | 2499359 | 8/2013 |
| JP | H0482919 | 3/1992 |
| JP | H04082918 | 3/1992 |
| JP | H04119121 | 4/1992 |
| JP | H09256226 A | 9/1997 |
| JP | 2004513250 A | 4/2004 |
| WO | 94/09190 | 4/1994 |
| WO | 2008/093342 | 8/2008 |
| WO | 2013050794 | 4/2013 |

OTHER PUBLICATIONS

Geunhyung Kim et al: "Alginate-Nanofibers Fabricated by an Electrohydrodynamic Process", Polymer Engineering and Science, Brookfield Center, US, Jan. 1, 2009 (Jan. 1, 2009), pp. 2242-2248, XP007910171, ISSN: 0032-3888, DOI: 10.1002/PEN.21472.
Database WPI Week 199217 Thomson Scientific, London, GB; AN 1992-138686 XP002731538.
Yimin Qin, Functional alginate fibres, chemical fibres international, Germany, Mar. 1, 2010, vol. 60 No. 1, 2010, 32-33.

* cited by examiner

METHOD OF PRODUCING A SWELLABLE POLYMER FIBRE

FIELD OF INVENTION

The present invention relates to a method of producing a swellable polymer fibre by extrusion or spinning and in particular, although not exclusively, to a swellable polymer fibre incorporating at least one antimicrobial agent for use in wound dressings.

BACKGROUND ART

Silver has long been established as having effective antimicrobial activity attributable to the oligodynamic effect where metal ions have a toxic effect on bacteria. Although the exact mechanism of toxicity is still uncertain, evidence suggests that silver ions denature enzymes of the target organism by binding to reactive groups and interfering with their metabolism.

Silver also has low toxicity in the human body and poses little risk when inhaled, ingested or applied to the skin and is used as an antimicrobial agent in a wide variety of applications including for example, incorporation into wound dressings. Such antimicrobial agents are often mixed with highly absorbent materials which collect the wound exudate. Silver is also used in creams, as an antibiotic coating on medical devices such as endotracheal tubes to reduce ventilator associated pneumonia and urinary catheters to reduce urinary tract infections. Silver is also employed as a water purification agent, for example within hospitals that filter hot water through copper and silver filters to decrease the risk of MRSA and legionella infections.

Other metals such as copper and its alloys are natural antimicrobial materials and control a wide range of moulds, fungi, algae and harmful microbes. Although the nature of the antimicrobial mechanism is uncertain, evidence suggests that elevated copper levels inside a cell causes oxidative stress, a decline in the membrane integrity and inappropriate binding to proteins which do not require copper for their function. Various studies have been conducted to investigate the antibacterial properties of copper touch surfaces, which may be introduced to door handles in hospitals to reduce the transmission of infection. Copper touch surfaces have been shown to significantly reduce the number of viable microbes such as *Escherichia Coli*, Methicillin-Resistant *Staphylococcus Aureus* (MRSA), *Clostridium difficile*, Influenza A and Adenovirus.

Zinc represents a further antimicrobial agent and is of biological importance exhibiting significant antimicrobial properties even at low concentrations. Zinc is commonly incorporated within topical ointments to protect against sunburn and is used in toothpaste to prevent halitosis and anti-dandruff shampoos. Zinc oxide nanoparticles have also been used within the linings of food cans and in packages of meat to extend shelf-life. Other metals also exhibit antimicrobial effects include gold, platinum, palladium, bismuth, tin and antimony.

There has been significant interest in incorporating such anti-microbial agents into wound dressings with the aim of releasing the antimicrobial agents into the wound site and promoting healing. Managing the wound environment and in particular wound exudate (produced as part of the healing process), is a constant challenge for healthcare professionals. The exudate plays several important roles in promoting healing, for example maintaining a moist environment necessary for cellular activity and carrying white blood cells to where they are most needed. Wound exudate is rich in leucocytes, proteases and growth factors which all work together to clear debris from the wound and promote new growth of tissue. While it is important to keep the wound moist, an overly wet environment may damage the wound bed. Therefore, effective management is needed by the application of wound dressings.

Alginates are often used as highly absorbent fibres to collect the wound exudate and by incorporating antimicrobial agents into the fibres, upon absorption of the wound exudate, ion-exchange takes place and releases the antimicrobial agent to assist in wound healing. A biofilm layer is often formed by wound bacteria as a defense against antimicrobials or adverse environmental factors, and can be difficult to breakdown, creating problems with delivering the target antimicrobial agents to the active site.

U.S. Pat. No. 5,888,526 describes that metal salts of organic compounds incorporated into fibrous material to inhibit mould and bacteria. In particular, Ag, Cu and Zn in combination with organic compounds such as pyrrole, pyrimidine, imidazole and thiazole are employed.

WO 2011/160862 is concerned with wound bandages for treatment of purulent and for prevention of suppurations of infected wounds. A nanostructured powder of bentonite intercalated by metal ions such as Ag, Cu and Zn is incorporated into a textile carrier for use as a wound dressing.

WO 2012/098298 discloses a non-woven fabric formed as a blend of at least two different fibre types. A first fibre is coated with elemental silver and a second fibre is essentially free from silver to provide mechanical strength. The fibres are bonded together by hydroentanglement.

US 2006/0149182 describes wound dressing materials comprising complexes of anionic polysaccharides with silver combined with a hydrocolloid adhesive. The dressing optionally incorporates other antimicrobial metal ions such as Bi, Cu, Ni, Zn, Mn, Mg and Au. The metallic ions may be maintained within compounds such as zeolite and hydroxyl apatite.

US 2008/0299160 explains a method of manufacture of polymer composites which incorporate metal nanoparticles for antimicrobial wound dressings.

US 2007/0275043 describes a wound contacting material incorporating a silver salt for delivering silver to a wound. The wound contacting material may take a number of forms, for example, alginate, chitosan, viscose, polyester, polyamide, polyethylene and polypropylene. In other embodiments, the material may also be selected from a foam or amorphous gel or collagen material. Alginate is preferred as an absorbent material for use in wound dressings to absorb wound exudate. Other water soluble polysaccharides may also be added to the material such as CMC, HPMC, pectin and other similar species and derivatives.

Fibres for use in the manufacture of wound dressings have been created using the well-established fibre spinning process that is a form of extrusion where a spinneret forms multiple continuous filaments which are then drawn to form a fibre. Four types of spinning methods are traditionally used for creating fibres: wet, dry, melt and gel.

The process of wet spinning involves the polymer being dissolved into a dope solution which is then forced under pressure through the spinneret submerged in a chemical coagulation bath. The filaments precipitate out of solution and are then drawn to form a fibre. Acrylic, rayon and spandex fibres are produced by this process. Dry spinning involves a similar process to wet spinning except the fibre is solidified through evaporation of the solvent and not coagulation. Melt spinning involves using polymers which do not require dissolution and are merely melted with the resulting fibre solidified on cooling. Gel spinning is a combination of wet and dry spinning and is often used to obtain high strength fibres. The polymer exists in a gel-like state which keeps the polymer chains partially bound together.

Metals in the form of salts or nanoparticles can be incorporated into such fibres in wet spinning by incorporating them in the dope solution or coagulation bath. However, there are often substantial problems associated with such techniques, including low solubility of the metal compounds in aqueous solution and displacement and precipitation reactions.

In particular, silver is typically incorporated in the dope solution, but this is often difficult due to the low solubility of silver compounds in aqueous solution. Some of the silver compound may not be fully incorporated into solution and the dope must be filtered in order to remove any precipitate before spinning can begin. As the spinneret is made from a series of small holes, clogging with precipitate during the spinning process is a particular problem. Accordingly, incorporating silver ions into a fibre using such spinning methodology is often expensive, inefficient and wasteful. Additionally, the efficiency of the spinning process is also largely dependent on the viscosity of the dope solution and at lower viscosity, the process is much more effective as the dope may pass through the spinneret with greater ease. This places an efficiency restraint on existing approaches that are not optimised in this respect.

SUMMARY OF THE INVENTION

The present invention aims to overcome the substantial problems of low solubility of the silver compounds in the aqueous dope solution. This is achieved, in part, by incorporated a glycol into the dope solution to aid solvation of the silver compounds. The presence of two hydroxyl groups increases hydrogen bonding and solubility.

The present invention also aims to increase the efficiency of the spinning process by the addition of a glycol to the dope solution which acts to decrease the viscosity. A further objective of the present invention is directed towards providing a method and a fibre for use in medical applications and in particular for the creation of medical grade fabrics, cloth, garments, bandages, clothing, and surgical wear and apparatus. The subject invention is also particularly beneficial for use as a wound dressing that exhibits enhanced levels of absorbency over existing systems. The absorbency of fibres, such as alginate, can be increased further by the addition of a glycol into the dope solution. It has been discovered that the presence of the glycol in the resulting fibres promotes absorption of wound exudate when applied to a wound dressing.

Preferably, the glycol (added to the dope solution) comprises 1,2-propanediol (typically referred to as propylene glycol or PG). Advantageously, 1,2-propanediol is non-toxic 'acutely' and is extensively metabolised by the liver.

Another aspect of this invention includes the incorporation of a lecithin, into the dope solution, to provide enhanced absorbency of the resultant fibre. Again, this is advantageous when preparing fibres for use in wound dressings particularly with regard to fibre shedding. Furthermore, lecithin is beneficial for spin finishing of fibres to prevent fibre breakage and eliminate or reduce as far as possible fibre shedding. These advantages are achieved specifically by including lecithin within the initial dope. The biofilm layer formed during the healing process often prevents delivery of the antimicrobial agents incorporated in the wound dressing to the active site. Advantageously, the presence of the lecithin in the resultant fibre facilitates the absorption of proteins from the wound exudate and may assist in the breakdown of the biofilm layer. The presence of the phosphoric acid functional group in lecithin is considered to reduce the pH of the resultant fibre and allow further effective delivery of the antimicrobial agents to the wound active site. Additionally, lecithin is advantageous when included in a fibre used as a wound dressing as the lecithin is more beneficial to the body then current spin finished fibres.

Another aspect of this invention includes a method of producing a swellable polymer fibre incorporating at least two antimicrobial metal ions by introduction via sequential coagulation baths. The desired antimicrobial metal ion can be incorporated into in-series-arranged (or sequential) coagulation baths to allow controlled addition to the fibre. Advantageously, by adopting such a technique, fewer undesirable displacement reactions occur and it is possible to control fully the magnitude of ion uptake within the fibre. This is a significant advantage economically as less of the silver compound incorporated in the dope solution will be displaced to the fibre surface and lost.

Preferably metal ions incorporated using the present method comprises silver, copper and zinc. The combination of using such metals is beneficial in producing effective antimicrobial fibres for use in wound dressings.

According to a first aspect of the present invention there is provided a method of forming a swellable polymer based fibre comprising: creating an aqueous dope solution containing a water soluble polymer; spinning or extruding the dope solution into a coagulation bath to form an extruded fibre; drawing the fibre from the coagulation bath; characterised by adding a glycol to the dope solution, the glycol having between two to fifteen carbon atoms.

The method may further comprise adding an antimicrobial agent to the dope solution; preferably the antimicrobial agent may comprise silver, a silver ion or a silver substrate. The method may also further comprise adding an antimicrobial agent to the coagulation bath. Preferably, the antimicrobial agent may comprise a metal ion selected from any one or a combination of the following set of: Zn, Cu, Ti, Pt, Pd, Bi, Sn, Sb. More preferably, the antimicrobial agent metal ion added to the coagulation bath is a combination of Cu and Zn.

Such antimicrobial agents may be in the form of elemental metals, metal salts, nanoparticles or metallic ions maintained in a compound such as zeolite or hydroxyl apatite.

The water soluble polymer may comprise any one or a combination of a polysaccharide or a hydrocolloid forming polymer, preferably in the form of pectin, alginate, *psyllium*, carboxymethylcellulose (CMC), konjac, aloe vera and/or chitosan.

Preferably, the glycol added to the dope solution comprises between two to fifteen carbon atoms. More preferably, the glycol comprises three carbon atoms. Even more preferably, the glycol is 1,2-propanediol.

The glycol is preferably added at a concentration of 0.05 to 40% by weight of the dope solution and more preferably at 0.05 to 20%, 0.05 to 15%, 0.05 to 10%, 0.05 to 8%, 0.05 to 5% and 0.05 to 3% by weight of the dope solution.

Preferably, the water soluble polymer comprises an alginate and more preferably high mannuronate content alginate (HM-alginate) alone or in combination with high guluronate content alginate (HG-alginate). Reference within the specification to 'high' mannuronate or guluronate refer to the mannuronate/guluronate ratio within the alginate where the HM-alginate refers to an alginate comprising a greater weight percent of mannuronate relative to guluronate content. Optionally, the HG-alginate:HM-alginate ratio may be in the range 1.5 to 2.4. These expressions also relate to the HM-alginate where the HG-alginate:HM-alginate ratio may be in the range 0.4 to 0.7. In particular, a HG-alginate may comprise 60 to 70% guluronate content and 30 to 40% mannuronate content. Additionally, a HM-alginate may comprise a 60 to 70% mannuronate content and 30 to 40% guluronate content.

Preferably, the method further comprises adding carboxymethyl cellulose (CMC), lecithin and/or psyllium to the dope solution.

According to a second aspect of the present invention there is provided a swellable fibre formed by a method of extrusion of a water soluble polymer comprising the steps of: creating an aqueous dope solution containing a water soluble polymer; spinning or extruding the dope solution into a coagulation bath to form an extruded fibre; drawing the fibre from the coagulation bath; characterised by: adding a glycol to the dope solution, the glycol having between two to fifteen carbon atoms.

Reference within the specification to a concentration by weight of a component of the dope solution may refer to weight percentage of the combined material added to the dope where the dope concentration is determined by the total weight of the dope solution and the total weight of components added to the dope solution. The weight percentage of various solid components identified within the specification therefore correspond to the weight percentage of one or more solids added to the dope solution referred to herein as the weight percentage of the dope solution. Optionally, the solids may be added to a glycol to form a glycol dispersion that is added to the dope. Optionally, the solids are added to the glycol at a combined amount of 5% w/w.

According to a third aspect of the present invention there is provided a swellable polymer based fibre comprising: a water soluble polymer selected from any one or a combination of a polysaccharide or a hydrocolloid forming polymer; characterised by: a glycol having between two to fifteen carbon atoms.

Preferably the glycol comprises three carbon atoms and more preferably is 1,2-propanediol.

The fibre may further comprise an antimicrobial agent metal ion selected from any one or a combination of the following set of: Ag, Zn, Cu, Ti, Pt, Pd, Bi, Sn, Sb. Preferably, the antimicrobial agent metal ion is a combination of Ag, Zn and Cu.

The water soluble polymer of the fibre preferably comprises any one or a combination of the following set of: pectin, alginate, psyllium, carboxymethylcellulose, konjac, aloe vera and/or chitosan. Preferably, the alginate is HM-alginate and/or HG-alginate.

Optionally, one or more components of the dope may be pre-soaked in glycol prior to introduction to the dope. Optionally, the water soluble polymer, psyllium and/or lecithin are pre-soaked in the glycol prior to introduction to the dope.

Optionally, the method comprises adding to the dope solution propylene glycol (5% by weight of the dope weight), the propylene glycol containing a 5% (w/w) solid comprising, and optionally consisting of HM alginate (75% to 85% by weight); lecithin (0.2% to 1.0% by weight) and CMC (15% to 30% by weight).

Preferably, the method comprises adding to the dope solution propylene glycol (5% by weight of the dope weight), the propylene glycol containing a 5% (w/w) solid comprising, and optionally consisting of HM alginate (78% to 81% by weight); lecithin (0.3% to 0.8% by weight) and CMC (17% to 23% by weight).

Optionally, the method comprises adding to the dope solution propylene glycol (5% by weight of the dope weight), the propylene glycol containing a 5% (w/w) solid comprising, and optionally consisting of psyllium (10% to 20% by weight); HM alginate (45% to 55% by weight); HG alginate (5% to 20% by weight); lecithin (0.2% to 1.0% by weight); CMC (15% to 35% by weight).

Preferably, the method comprises adding to the dope solution propylene glycol (5% by weight of the dope weight), the propylene glycol containing a 5% (w/w) solid comprising, and optionally consisting of psyllium (12% to 17% by weight); HM alginate (48% to 52% by weight); HG alginate (7% to 13% by weight); lecithin (0.3% to 0.8% by weight); CMC (22% to 28% by weight).

Optionally, silver may be added to the dope and/or the coagulation bath in the form of a salt.

Optionally, the as-formed fibre comprises any one or a combination of psyllium (trace to 20% by weight), CMC (5 to 30% by weight), propylene glycol (1 to 10% by weight), lecithin (0.1 to 2.0% by weight), HM alginate (40 to 100% by weight) and HG alginate (0 to 40% by weight). Preferably, the swellable fibre comprises HM alginate, glycol, psyllium, lecithin, CMC and HG alginate.

Reference within this specification to a swellable fibre' encompass a fibre being partially crystalline and in particular mostly or predominantly crystalline. The term also encompasses a fibre comprising predominantly orientated crystals, with the crystals aligned substantially relative to one another. Optionally, the present swellable fibres are extruded optionally with or without twisting.

Optionally, lecithin is added at trace to 40%, 0.05% to 10% and more preferably 0.1 to 1% by weight of solid added to the dope solution. Optionally, psyllium is added at trace to 20%, 5% to 20%, 10% to 20% or 11% to 16% by weight of solid added to the dope solution.

According to a forth aspect of the present invention there is provided a method of forming a swellable polymer based fibre comprising: creating an aqueous dope solution containing a water soluble polymer; spinning or extruding the dope solution into a coagulation bath to form an extruded fibre; drawing the fibre from the coagulation bath; characterised by: adding a lecithin to the dope solution.

Preferably, the lecithin is L-alpha-lecithin.

The method may further comprise adding a metal based antimicrobial agent to the dope solution. Preferably, the antimicrobial agent comprises silver, a silver ion or a silver substrate.

The method may further comprise adding a metal based antimicrobial agent to the coagulation bath. Preferably, the antimicrobial agent is a metal ion selected from any one or a combination of the following set of: Zn, Cu, Ti, Pt, Pd, Bi, Sn, Sb. More preferably, the antimicrobial agent metal ion is Zn and Cu.

The method may further comprise adding a glycol to the dope solution. Preferably, the glycol comprises between two and fifteen carbon atoms and more preferably, the glycol comprises three carbon atoms. Even more preferably, the glycol is 1,2-propanediol.

The water soluble polymer may comprise any one or a combination of a polysaccharide or a hydrocolloid forming polymer. Preferably, pectin, alginate, psyllium, carboxymethylcellulose, konjac, aloe vera and/or chitosan.

According to a fifth aspect of the present invention there is provided a swellable fibre formed by a method of extrusion of a water soluble polymer comprising the steps of: creating an aqueous dope solution containing a water soluble polymer; spinning or extruding the dope solution into a coagulation bath to form an extruded fibre; drawing the fibre from the coagulation bath; characterised by: adding a lecithin to the dope solution.

According to a sixth aspect of the present invention there is provided to a swellable polymer based fibre comprising: a water soluble polymer selected from any one or a combination of a polysaccharide or a hydrocolloid forming polymer incorporating at least one antimicrobial agent, characterised by: a lecithin.

Preferably, the antimicrobial agent is a metal species selected from any one or a combination of the following set: Ag, Zn, Cu, Ti, Pt, Pd, Bi, Sn, Sb. More preferably, the antimicrobial agent metal ion is a combination of Ag, Zn and Cu.

The water soluble polymer may comprise any one or a combination of a polysaccharide or a hydrocolloid forming polymer. Preferably, the water soluble polymer may comprise any one or a combination of pectin, alginate, *psyllium*, carboxymethyl cellulose, konjac, aloe vera and/or chitosan.

The method may further comprise adding a glycol to the dope solution. Preferably, the glycol is between two and fifteen carbon atoms and more preferably, the glycol is three carbon atoms. Even more preferably, the glycol is 1,2-propanediol.

According to a seventh aspect of the present invention there is provided a method of forming a swellable polymer based fibre comprising: creating an aqueous dope solution containing a water soluble polymer; spinning or extruding the dope solution into a first coagulation bath to form an extruded fibre; characterised by: drawing the fibre from the first coagulation bath into a second coagulation bath and drawing the fibre from the second coagulation bath.

The method may further comprise adding an antimicrobial agent to the dope solution. Preferably, the antimicrobial agent comprises silver, a silver ion or a silver substrate. Preferably, the first coagulation bath contains at least one antimicrobial agent. More preferably, the antimicrobial agent in the first coagulation bath is a metal species comprising any one or a combination of the set of: Zn, Cu, Ti, Pt, Pd, Bi, Sn, Sb.

Preferably, the second coagulation bath contains at least one antimicrobial agent. More preferably, the antimicrobial agent in the second coagulation bath is a metal species comprising any one or a combination of the set of: Zn, Cu, Ti, Pt, Pd, Bi, Sn, Sb.

Preferably, the combination of the antimicrobial metal species in the first and second coagulation baths is Zn and Cu.

The method may further comprise drawing the fibre from the second coagulation into at least one other subsequent coagulation bath. Preferably, the at least one other subsequent coagulation bath contains at least one antimicrobial metal ion selected from Zn, Cu, Ti, Pt, Pd, Bi, Sn, Sb.

The method may further comprise adding a glycol to the dope solution. Preferably, the glycol comprises between two and fifteen carbon atoms. More preferably, the glycol comprises three carbon atoms. Even more preferably, the glycol is 1,2-propanediol. The method may further comprise adding a lecithin to the dope solution. Preferably, the lecithin is L-alpha-lecithin.

The polymer may preferably comprise any one or a combination of a polysaccharide or a hydrocolloid forming polymer. More preferably, the polymer comprises pectin, alginate, *psyllium*, carboxymethylcellulose, konjac, aloe vera and/or chitosan.

According to an eighth aspect of the present invention there is provided a swellable fibre formed by a method of extrusion of a water soluble polymer comprising the steps of: creating an aqueous dope solution containing a water soluble polymer; spinning or extruding the dope solution into a first coagulation bath to form an extruded fibre; characterised by: drawing the fibre from the first coagulation bath into a second coagulation bath and drawing the fibre from the second coagulation bath.

BRIEF DESCRIPTION OF DRAWINGS

A specific implementation of the present invention will now be described, by way of example only, and with reference to the accompanying drawings in which.

DETAILED DESCRIPTION OF PREFERRED EMBODIMENT OF THE INVENTION

Figure 1:
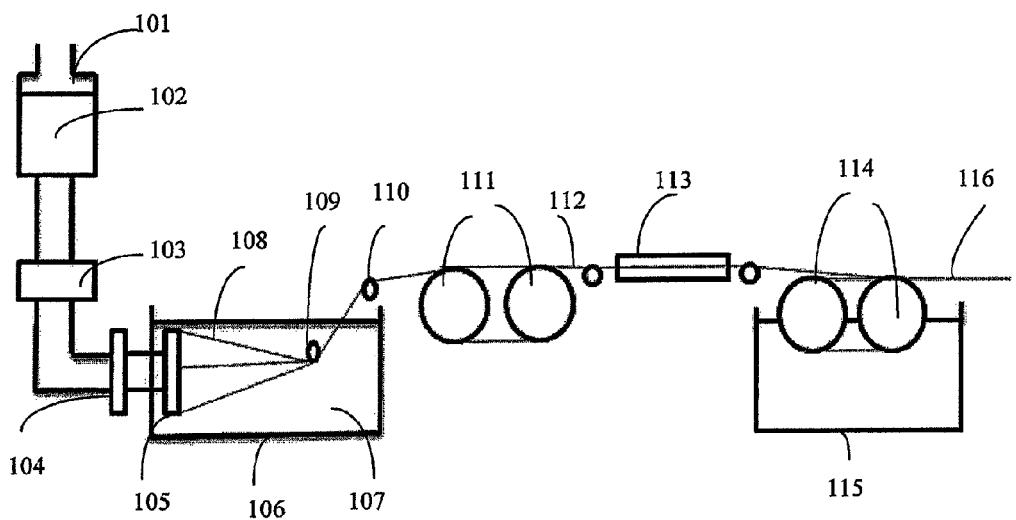
FIG. 1 shows a cross-sectional view of apparatus used in wet spinning a swellable polymer fibre with a single coagulation bath according to a specific implementation of the present invention.

Referring to FIG. 1, swellable polymer fibres are produced by first dissolving a polymer species in water to form a dope solution 102. The dope solution is contained within a vessel 101 under an inert atmosphere. The dope solution 102 is then passed directly through a pump 103 which increases the pressure of the system. The dope solution 102 is then filtered by a filter 104, before entering a spinneret head 105. The spinneret head 105 is immersed in the coagulant 107 contained within a coagulation bath 106. Dope solution 102 is then extruded into coagulation bath 106 to form fibre filaments 108 which are then hauled-off over filament guides 109 and 110 from bath 106 by means of first advancing rollers 111. The resulting fibres 112 are then passed through orientation bath 113 containing hot water whilst being drawn by second advancing rollers 114 within a wash bath 115 to form a resulting fibre 116.

Figure 2:
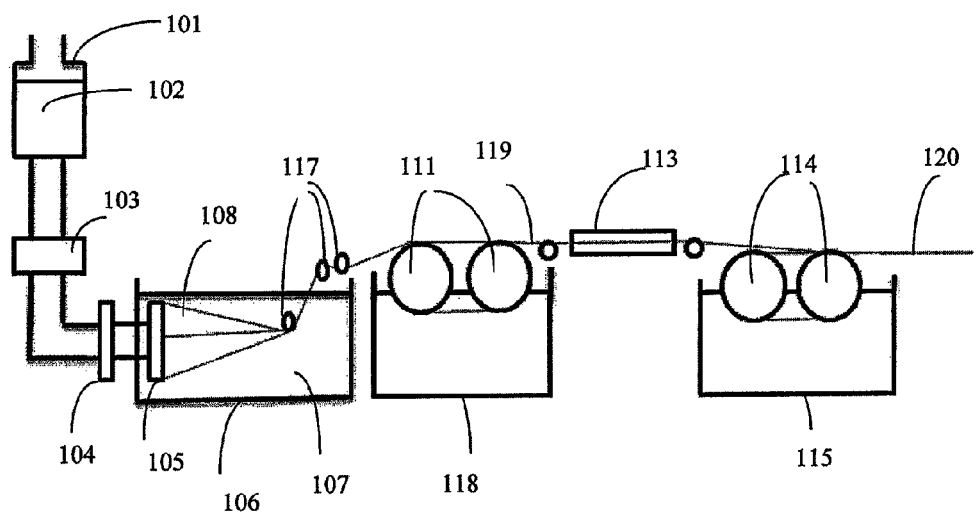
FIG. 2 shows a cross-sectional view of apparatus used in wet spinning a swellable polymer fibre using two coagulation baths coupled in-series according to a further specific implementation of the present invention.

As a modification to the apparatus and method of FIG. 1, according to a further embodiment shown in FIG. 2, the swellable polymer fibres are passed through a second coagulation bath 118 after passing between a set of three guide rollers 117 to remove tow excessive coagulant from bath 106. The fibres are slightly stretched as they pass between the first coagulation bath 106 and enter second coagulation bath 118 via means 111. The resulting fibres 119 are then passed through orientation bath 113 containing hot water and then further drawn by means 114 within wash bath 115 to form the resulting fibre 120.

EXPERIMENTAL

Within the following examples 1 to 13, the amount of solid added to the dope is expressed as a weight percentage of the weight of the dope.

Example 1

Calcium alginate polymer fibres containing 1,2-propanediol were produced using the method described with reference to FIG. 1. A 1500 g dope solution was prepared using 5% (w/w) High G sodium alginate (Protanal LF 10/60 FT) and 10% (w/w) propylene glycol, PG (supplied by Sigma-Aldrich, by 187° C. density 1.036 g/cm$^3$) The alginate used was supplied by FMC Biopolymer (UK) Ltd) and had the following characteristics: guluronic acid content 60-70%; mannuronic acid content 30-40%; G/M ratio 1.5-2.33, viscosity (1%) 30-60 cps, moisture <15% and pH 6-8. The required amount of the alginate powder (75 g) was first dissolved in 1275 g of water for 30 minutes using a Greaves high shear mixer. Then, 150 g of PG was slowly added and further stirred for 30 minutes or until fully mixed and homogeneous dope. (viscosity 8,000-10,000 cps at 26° C. using Brookfield Digital viscometer (RVTD), spindle No. 04). The solution was slowly fully vacuum de-aerated, spun through a cartridge filter (25-microns) and spinneret (70μ hole size/2000 holes) into 1.5-2% aqueous calcium chloride dihydrate. After coagulation, the fibres were stretched and washed to give strong propylene glycol-calcium alginate fibres.

Example 2

Calcium alginate and *psyllium* polymer fibres containing 1,2-propanediol were produced using the method described with reference to FIG. 1.

A spinning solution (6,000 g) was prepared comprising 240 g (4% w/w) High M sodium alginate, 45 g (0.75% w/w) *psyllium* husks (*Plantago ovate*, supplied by W. Ratje Froeskaller ApS Husk Products, Kirstinehoej 34, DK-2770 Kastrup, Denmark) and 120 g (2% w/w) PG. The high M alginate (Manucol DH) was supplied by FMC Biopolymer (UK) Ltd) and had the following characteristics: mannuronic acid content 60-70%; guluronic acid content 30-40%; G/M ratio 0.43-0.67, viscosity (1%) 40-90 cps, moisture <13% and pH (1% solution) 5.0-7.5.

First, the *psyllium* was soaked in about 5,600 g of water for 1 hour at room temperature and at the end filtered through a Philips blender cartridge filter. The filtered aqueous *psyllium* solution was then stirred vigorously using a high shear mixer whilst gradually adding the alginate powder. The alginate was allowed to dissolve well (30-45 minutes) before gradually adding PG and further mixing (20-30 minutes) to obtain a homogeneous dope (viscosity 8,000-15,000 cps at 26° C.). The dope was spun after vacuum deaeration and filtration through a spinneret (70μ/2000 holes) into 1.5-2% aqueous calcium chloride dihydrate. After coagulation, the fibres were stretched and washed to give strong absorbent calcium alginate/PG/*psyllium* fibres.

Example 3

Calcium alginate and *psyllium* polymer fibres containing 1,2-propanediol and antimicrobial silver ions were prepared using the method described with reference to FIG. 1.

Example 2 was repeated except that the dope contained 3 g (0.05% w/w) silver carbonate. The silver carbonate can be dispersed in water by sonicating for 1 hour in ultrasonic bath before mixing into the filtered *psyllium* solution. However, in this example, the carbonate was dispersed in PG, sonicated briefly (10 minutes) before adding to the dope. After deaeration and filtration, the dope was spun through a 90μ/2000-hole spinneret.

Example 4

Calcium alginate and carboxymethylcellulose (CMC) polymer fibres containing 1,2-propanediol and antimicrobial silver ions were produced using the method described with reference to FIG. 1.

The process corresponded to examples 3 and 4 except that the dope contained 30 g (0.5% w/w) of CMC instead of *psyllium*. The GPA grade CMC powder (degree of substitution 0.82-0.95; pH 6.5-8.5 and supplied by Dow Wolff Cellulosics GmbH) was mixed with the 240 g sodium alginate powder before dissolving in 5607 g of water.

Example 5

Calcium alginate and pectin polymer fibres containing 1,2-propanediol and antimicrobial silver ions were produced using the method described with reference to FIG. 1.

The process involved the same components and steps as Example 4 but using pectin instead of CMC.

Example 6

Alginate polymer fibres containing antimicrobial silver, copper and zinc ions were produced following using the method described with reference to FIG. 2.

This example describes the production of antimicrobial alginate fibres containing 6% Cu, 4-5% Zn and 0.6% Ag. Initially, 500 g dope was prepared by mixing together 20 g (4% w/w) High G sodium alginate (Protanal LF 10/60 FT supplied by FMC Biopolymer (UK) Ltd) and 0.25 g (0.05% w/w) each of silver nitrate, copper chloride and zinc chloride in 479.25 g water. The alginate supplied had the following characteristics: guluronic acid content 60-70%; mannuronic acid content 30-40%; G/M ratio 1.5-2.33, viscosity (1%) 30-60 cps, moisture <15% and pH 6-8.

However, the dope prepared from this combination was brittle, viscous, light green in appearance and considerably difficult to extrude due to filtration problems. Further attempts were made with varying proportions of the salts in the dope but not much success was achieved with extrusion. However, when the same weight of dope was prepared with only silver nitrate or silver carbonate and spun through 90μ/2000-hole spinneret into successive baths containing respectively aqueous solutions of 0.5% copper chloride dihydrate and 1.5% zinc chloride, no difficulties were experienced, thus establishing the best practical approach to incorporate all the three metal ions into the fibres.

After coagulation, the fibres were stretched and washed to give strong silver alginate fibres containing copper and zinc, with the amounts of the metals ions in the fibre depending almost entirely on the coagulant concentrations. Consequently, it was necessary during extrusion to ensure consistent concentrations of the salts in their respective coagulation baths through reduction of coagulant cross contamination and mass balancing Example 7

Alginate polymer fibres containing 1,2-propanediol and antimicrobial silver, copper and zinc ions were produced using the method described with reference to FIG. 2.

This example describes the production of antimicrobial propylene glycol alginate fibres containing 8-9% Zn, 0.5-1% Cu and 0.5% Ag. A 1500 g dope solution was prepared using 75 g (5% w/w) High G sodium alginate (Protanal LF 10/60 FT), 150 g (10% w/w) propylene glycol, PG (supplied by Sigma-Aldrich, by 187° C. density 1.036 g/cm$^3$) and 3 g (0.05% w/w) silver carbonate. The required amount of the alginate powder was first dissolved in 1275 g of water for 30 minutes using a high shear mixer. The silver carbonate powder was dispersed in PG by sonicating briefly (10 minutes) in an ultrasonic bath before adding slowly to the dope whilst stirring vigorously. After the addition, the dope was mixed for a further 45 minutes, then vacuum de-aerated and filtered under pressure through a 25μ cartridge filter before extruding through a 90μ/2000-hole spinneret into two successive coagulations baths—the first bath containing 1.5% zinc chloride and the second bath 0.05-0.15% copper chloride. After coagulation, the fibres were stretched and washed to give strong zinc alginate fibres containing copper and silver.

Example 8

Alginate and *psyllium* polymer fibres containing 1,2-propanediol and antimicrobial silver, copper and zinc ions were produced using the method described with reference to FIG. 2.

This example describes the production of fibres containing ~5% Zn, ~6% Cu and 0.5% Ag. Example 6 was repeated except that the dope also contained about 11.25 g (0.75% w/w) *psyllium* husk (*Plantago ovate*, supplied by W. Ratje Froeskaller ApS Husk Products, Kirstinehoej 34, DK-2770 Kastrup, Denmark) and a reduced amount of sodium alginate, 60 g (4% w/w) and PG, 30 g (2% w/w). The 11.25 g *psyllium* were soaked in 1415 g water for 1 hour at room temperature and at the end filtered through a Philips blender cartridge filter. The filtered aqueous *psyllium* solution was then stirred vigorously using a high shear mixer whilst gradually adding the alginate powder. The alginate was allowed to dissolve well (30-45 minutes) before gradually adding PG containing 3 g (0.05%) silver carbonate which had been previously dispersed in the glycol by sonicating in ultra-sonic bath. The components were continuously mixed until a homogeneous dope was obtained (1 hour). After deaeration and filtration, the dope was spun through a spinneret (70μ/2000 holes) into two successive coagulations baths—the first bath containing 1.5% zinc sulphate and the second bath 0.5% copper chloride. After coagulation, the fibres were stretched and washed to give strong zinc alginate/*psyllium*/PG fibres containing copper and silver.

Example 9

Alginate and CMC polymer fibres containing 1,2-propanediol and antimicrobial silver, copper and zinc ions were produced using the method described with reference to FIG. 2.

Example 7 was repeated except that the dope contained 15 g (1.0% w/w) of CMC mixed with alginate powder before dissolution.

Example 10

Calcium alginate polymer fibres containing 1,2-propanediol and lecithin were produced following the method described with reference to FIG. 1.

A dope (1000 g) was prepared using 4% (w/w) High M sodium alginate (Manucol DH supplied by FMC Biopolymers, UK, Ltd), 10% (w/w) propylene glycol, PG (supplied by Sigma-Aldrich) and 0.05% granular L-alpha-lecithin (supplier—Across Organics). The required amount of the alginate powder (75 g) was mixed with 0.5 g of lecithin and dissolved in about 900 g of water for 45 minutes using a high shear mixer. Then, 100 g of PG was slowly added and further stirred for 30 minutes or until fully mixed and a homogeneous dope was formed (viscosity 8,000-10,000 cps at 26° C. using Brookfield Digital viscometer (RVTD), spindle No. 04). The solution was slowly fully vacuum de-aerated, spun through a cartridge filter (25-microns) and spinneret (90μ hole size/35 holes) into 1.5% aqueous calcium chloride dihydrate solution. After coagulation, the fibres were stretched and washed to give strong propylene glycol-lecithin alginate fibres.

Example 11

Calcium alginate and *psyllium* polymer fibres containing 1,2-propanediol and lecithin were produced following the method described with reference to FIG. 1.

A spinning solution (6000 g) was prepared by first soaking 60 g (0.5%) of *psyllium* husks in 5394 g of water for 2 hours and filtering the mixture through a 75-micron mesh. This was followed by mixing sodium alginate powder (Protanal LF 10/60 FT), 240 g (4% w/w) with 6 g (0.5% w/w) of granular L-alpha-lecithin. The filtered aqueous *psyllium* solution was then stirred vigorously using a high shear mixer whilst gradually adding the mixed powders. Stirring was continued for 30 minutes before gently adding 300 g (5% w/w) PG and further mixing (30 minutes) to obtain a homogeneous dope (viscosity 10,000-15,000 cps at 26° C.) suitable for extrusion. The dope was spun after vacuum deaeration and filtration through a spinneret (70μ/2000 holes) into 1.5-2% aqueous calcium chloride dihydrate. After coagulation, the fibres were stretched and washed to give strong absorbent fibres.

Example 12

Alginate and *psyllium* polymer fibres containing 1,2-propanediol, lecithin and antimicrobial silver ions were produced using the method described with reference to FIG. 1.

Example 11 was repeated except that the dope contained 3 g (0.05% w/w) silver carbonate; the silver carbonate being dispersed in PG before adding.

Example 13

Alginate, CMC and *psyllium* polymer fibres containing 1,2-propanediol, lecithin and antimicrobial silver, copper and zinc metal ions were produced following the method described with reference to FIG. 2.

A dope (6000 g) contained 240 g (4% w/w) of sodium alginate, 30 g (0.5% w/w) of CMC, 3 g (0.05% w/w) of lecithin, 36 g (0.6% w/w) of *psyllium*, 120 g (2% w/w) of propylene glycol and silver carbonate (3 g, 0.5% w/w). First, the *psyllium* was soaked for 1 hour in 5568 g of water and filtered at the end through a 75-micron mesh. The sodium alginate, CMC and lecithin powders were mixed together and gradually added to the *psyllium* solution stirred vigorously by a high shear mixer. The powders were allowed to dissolve well (45 minutes) before gradually adding PG containing properly dispersed silver carbonate. The components were continuously mixed until a homogeneous dope was obtained (45 minutes). After deaeration and filtration, the dope was spun through a spinneret (70μ/2000 holes) into two successive coagulations baths—the first bath containing 1.5% zinc sulphate and the second bath 0.5% copper chloride. After coagulation, the fibres were stretched, washed and dried to give good absorbent fibres suitable for wound dressing.

Examples 14 to 20

Highly swellable fibres with varying integrities were prepared using the component concentrations detailed below in examples 14 to 20. In each example, a dope of 2500 g with a solid content of 5% w/w was prepared. In examples 14 to 20, the amount of solid added to the dope is expressed as a percentage by weight of the total amount of solid added to the dope solution where the total amount of solid added was 5% by weight. The solids according to examples 14 to 20 include any one of alginate, HM-alginate, HG-alginate, *psyllium*, CMC, lecithin. Referring to example 14 below, the HM alginate was dispersed in 10% propylene glycol (PG), stored for 1 hour and then added to the water used to prepare the dope. No lecithin, *psyllium*, HG-alginate or CMC was added. The relative amount of the components of example 14 include: a dope weight 2500 g; dope concentration 5%; HM-alginate 125 g; PG 250 g and water (85%) 2125 g.

However, for the remaining examples 15 to 20, all solids (where appropriate) were first prepared prior to introduction to the dope by dispersion within propylene glycol (PG) with the glycol/solids dispersion allowed to stand for at least one hour before mixing into the aqueous dope and stirring 45 minutes to one hour until a homogenous dope was obtained. The concentrations of examples 14 to 20 are shown in table 1.

TABLE 1 compositions of examples 14 to 20

| Example | Composition | Percentage in 5% solid content P/HM/HG | LE | CMC | % PG in dope | Dope viscosity cP |
|---|---|---|---|---|---|---|
| 14 | AF-PG-140703-HM | 0/100/0 | — | — | 10 | 18,920 |
| 15 | *AF-140704-PG-HM | 0/100/0 | — | — | 10 | 14,840 |
| 16 | AF-PG-LE-140714-HM | 0/99.4/0 | 0.6 | — | 5 | 12,160 |
| 17 | AF-CMC-PG-LE-140804-HM | 0/79.4/0 | 0.6 | 20 | 5 | 10,480 |
| 18 | AF-CMC-PG-LE-140806-HM/HG | 0/45/30 | 0.6 | 24.4 | 5 | 10,680 |
| 19 | PF-CMC-PG-LE-140807-HM/HG | 13.4/41/20 | 0.6 | 25 | 5 | 13,440 |
| 20 | PF-CMC-PG-LE-140812-HM/HG | 14.4/50/10 | 0.6 | 25 | 5 | 11,880 |

AF—Alginate fibre without psyllium;
PF—alginate fibre with psyllium;
P—psyllium;
HM—High M Na-alginate (Manucol DH);
HG—High G Na-alginate (Protanal LF 10/60FT)
*Alginate dissolved before addition of PG Performance Testing The viscosity of the dope solution was measured using a Brookfield digital viscometer (RVTD) and RV spindle size 04 at 25° C. Selected fibres from the examples cited were tested as follows:

Liquid Absorption Properties of the Fibre Samples

The liquid absorption properties of the fibres prepared were assessed in saline (9 g, 0.9% w/v NaCl in 1 liter de-ionized water) and in solution A (mixed $CaCl_2.2H_2O$ and NaCl solution containing 142 mmol/liter $Na^+$ ions, 8.298 g NaCl and 2.5 mmol/liter of $Ca^{2+}$ ions, 0.368 g $CaCl_2.2H_2O$).

a) Absorbency

Absorbency was determined by fully immersing 1.0 g fibre sample in 100 g saline or solution A contained in a Petri dish and allowing to stand for 30±1 min in oven at 37° C. The sample was removed, then allowed to drain for 30 seconds and weighed. Absorbent capacity (g/g) was calculated as the ratio of the wet weight ($W_1$) of the fibre to the dry weight ($W_0$) at ambient temperature.

b) Liquid Uptake (Retention)

Liquid uptake is expressed as $(W_1-W_2)/W_2$ and was determined as follows: The wet weight ($W_1$) is the weight after a 1.0 g sample has been immersed in 100 g of deionised water or saline or solution A for at least 30 minutes in an oven at 37° C., then removed and allowed to drain for 30 seconds. The dry weight ($W_2$) is the weight after the wet sample (centrifuged at 1500 rpm for 15 min) has been dried in an oven for at least 4 hr at 105° C. From these weights the water, saline or 'solution A' uptake (retention) was calculated.

Silver Content of Fibres and Competitive Wound Dressings (at Intertek ASG)

Duplicate 0.5 g quantities of each sample were placed in a quartz microwave digestion vessel and digested with nitric and sulphuric acid. After digestion samples were transferred to 50 ml volumetric flasks and made up to volume with deionized water. Sample solutions were analysed by ICP-OES for silver.

Silver Release from Fibres and Competitive Wound Dressings (at Intertek ASG)

Samples were weighed into separate 50 ml plastic centrifuge tubes and a 25 ml aliquot of broth solution was added. At each time point (1, 24, 48, and 72 h) the spent broth solution was decanted into new 50 ml plastic centrifuge tubes and stored for analysis. Once all broth solutions had been collected, they were centrifuged at 45,000 rpm for 15 mins and diluted further by taking 1 ml of the broth solution and making up to a total volume of 10 ml in plastic vials containing internal standard. All the broth solutions were analysed together by ICP-MS against standards of known silver concentrations (0.2, 0.5, 1, 2 and 5 ppm w/v). The reported results were normalized for a standard weight of 0.5000 g.

Antimicrobial Effectiveness of Fibres and Competitive Wound Dressings (at Surgical Materials Testing Laboratory)

A known weight (0.2-0.3 g) of the test material was placed in 10 ml of simulated wound fluid (50% serum/50% maximum recovery diluent) inoculated with a known number of micro-organisms and gently shaken at 35° C. Aliquots were removed at selected time points (0, 4, 24, 48, 72 h) and the organisms counted. Results are presented as either number of actual organisms or percentage reduction compared with the initial inoculum, and log reduction (Note: the initial microbial population was $2.25 \times 10^6$ cfu/ml for MRSA and $1.59 \times 10^6$ cfu/ml for *Pseudomonas aeruginosa*).

Antibacterial Activity Assessment of Fibre Samples: Zone of Inhibition

The method of assessment was based on the standard method outlined in AATCC TM 147-2004 using *Staphylococcus aureus* (Gram positive) and *Klebsiella pneumoniae* (Gram negative) as test bacteria.

The zone of inhibition (ZOI) defined as 'clear area of no growth of a microorganism, cultured onto the surface of an agar growth medium, in proximity to the borders of a specimen placed in direct contact with this agar surface' was evaluated using the simple equation: $W=(T-D)/2$; where W is the width of clear zone of inhibition in μm or mm T is the total diameter of test specimen and clear zone in μm or mm.

Results

The Fibre absorbency of the calcium alginate and *psyllium* polymer fibres containing 1,2-propanediol of example 2 was: saline 30-50 g/g.

The test results of the Calcium alginate and *psyllium* polymer fibres containing 1,2-propanediol and antimicrobial silver ions of example 3 were: Fibre absorbency: saline 37 g/g; Silver content of the fibre: 0.6%; Zone of inhibition: 2221 μm for *S. aureus* and 883 μm for *Klebsiella*.

The test results of the alginate and *psyllium* polymer fibres containing 1,2-propanediol and antimicrobial silver, copper and zinc ions of example 8 were: Fibre absorbency: saline 22-25 g/g; Zone of inhibition (24 h): 1924 μM for *S. aureus* and 3796 μm for *Klebsiella*. Percentage reduction (72 h-7 days): 99.99% for MRSA and *Pseudomonas aeruginosa*.

The test results of a comparison fibre batch containing Aquacel Ag fibres were: Fibre absorbency: 20-22 g/g; Zone of inhibition: 2796 μm for *S. aureus* and 1150 μm for *Klebsiella*. Percentage reduction (72 h-7 days): 99.99% for MRSA and *Pseudomonas aeruginosa*.

These results suggest that the fibres produced following the method described with reference to FIG. 2 resulted in fibres which were almost equally effective against both gram negative and positive microbes. This is not always the case with most available commercial antimicrobial wound dressings.

The test results of the Alginate, CMC and *psyllium* polymer fibres containing 1,2-propanediol, lecithin and antimicrobial silver, copper and zinc metal ions of example 8 were Fibre absorbency: saline 30-35 g/g; Zone of inhibition: 2348 μm for *S. aureus* and 2308 μm for *Klebsiella*.

The absorbency in 'solution A' of the swellable fibres produced by examples 14 to 20 in addition to the retention performance (liquid uptake) are detailed in table 2

TABLE 2

Absorbency and retention performance results for examples 14 to 20

| | | Solution A | |
|---|---|---|---|
| Example | Composition | Absorbency g/g | Retention g/g |
| 14 | AF-PG140703-HM | 16.36 | 19.59 |
| 15 | *AF-140704-PG-HM | 14.98 | 18.11 |
| 16 | AF-PG-LE-140714-HM | 18.67 | 22.27 |
| 17 | AF-CMC-PG-LE-140804-HM | 30.60 | 36.54 |
| 18 | AF-CMC-PG-LE-140806-HM/HG | 23.92 | 29.00 |
| 19 | PF-CMC-PG-LE-140807-HM/HG | 26.40 | 32.65 |
| 20 | PF-CMC-PG-LE-140812-HM/HG | 31.65 | 37.00 |

AF—Alginate fibre without psyllium;
PF—alginate fibre with psyllium;
P—psyllium;
HM—High M Na-alginate (Manucol DH);
HG—High G Na-alginate (Protanal LF 10/60FT)
*Alginate dissolved before addition of PG

The invention claimed is:

1. A method of forming a swellable polymer based fibre comprising:
    creating an aqueous dope solution containing a water soluble polymer;
    spinning or extruding the dope solution into a coagulation bath to form an extruded fibre;
    drawing the fibre from the coagulation bath;
    adding a glycol to the dope solution, the glycol having between two to fifteen carbon atoms; and
    adding a lecithin to the dope solution.

2. The method as claimed in claim 1 further comprising adding a metal based antimicrobial agent to the dope solution.

3. The method as claimed in claim 2 wherein the antimicrobial agent comprises silver, a silver ion or a silver substrate.

4. The method as claimed in claim 1 further comprising adding a metal based antimicrobial agent to the coagulation bath.

5. The method as claimed in claim 4 wherein the antimicrobial agent is a metal ion selected from any one or a combination of the following set of:
    Zn, Cu, Ti, Pt, Pd, Bi, Sn, Sb.

6. The method as claimed in claim 1 wherein the polymer comprises any one or a combination of a polysaccharide or a hydrocolloid forming polymer and optionally pectin, alginate, *psyllium*, carboxymethylcellulose, konjac, aloe vera and/or chitosan.

7. The method as claimed in claim 1 wherein the glycol comprises between two to fifteen carbon atoms.

8. The method as claimed in claim 1 wherein the glycol is added at a concentration of 0.05 to 10% by weight of the dope solution.

9. The method as claimed in claim 1 further comprising adding any one or a combination of the following to the dope solution:
    *psyllium*
    carboxymethylcellulose
    high mannuronate content alginate
    high guluronate content alginate.

10. The method as claimed in claim 1 wherein the lecithin is added at a concentration of 0.05 to 10% by weight of the dope solution.

* * * * *